(12) United States Patent
Sharma et al.

(10) Patent No.: US 12,310,558 B2
(45) Date of Patent: May 27, 2025

(54) MEDICAL ARTICULATION DEVICES AND METHODS OF USING THE SAME

(71) Applicant: Boston Scientific Limited, Galway (IE)

(72) Inventors: Deepak Kumar Sharma, Muzaffarnagar (IN); James J. Scutti, Norwell, MA (US); Sharath Kumar G, Kanakapura (IN)

(73) Assignee: Boston Scientific Limited, Galway (IE)

( * ) Notice: Subject to any disclaimer, the term of this patent is extended or adjusted under 35 U.S.C. 154(b) by 280 days.

(21) Appl. No.: 17/480,330

(22) Filed: Sep. 21, 2021

(65) Prior Publication Data

US 2022/0087504 A1 Mar. 24, 2022

Related U.S. Application Data

(60) Provisional application No. 63/081,795, filed on Sep. 22, 2020.

(51) Int. Cl.
*A61B 1/005* (2006.01)
*A61B 1/018* (2006.01)
*A61B 17/29* (2006.01)

(52) U.S. Cl.
CPC .......... *A61B 1/0053* (2013.01); *A61B 1/0057* (2013.01); *A61B 1/018* (2013.01);
(Continued)

(58) Field of Classification Search
CPC ..... A61B 1/0053; A61B 1/0057; A61B 1/018; A61B 2017/003; A61B 2017/00323; A61B 2017/00424; A61B 2017/291; A61B 17/2909; A61B 17/29; A61B 17/00234; A61B 1/005; A61B 1/0051; A61B 1/0052; A61B 1/0055; A61B 1/0056; A61B 1/0058; A61B 2017/00318; A61B 2017/00327; A61M 25/0133; A61M 25/0136; A61M 25/0147; A61M 2017/2905; A61M 2017/2908; A61M 2017/291; A61M 2017/2918
See application file for complete search history.

(56) References Cited

U.S. PATENT DOCUMENTS 4,178,920 A * 12/1979 Cawood, Jr. ...... A61M 25/0147
74/502
5,397,304 A * 3/1995 Truckai ............. A61M 25/0147
604/528
(Continued)

FOREIGN PATENT DOCUMENTS

WO WO-2020165947 A1 * 8/2020 ........... A61B 1/0052

OTHER PUBLICATIONS

International Search Report and Written Opinion issued on Nov. 16, 2021, in counterpart International Patent Application No. PCT/IB2021/058598 (12 pages, in English).

*Primary Examiner* — Ryan N Henderson
(74) *Attorney, Agent, or Firm* — Bookoff McAndrews PLLC (57) ABSTRACT

A medical device that includes a handle, a shaft extending distally from the handle, an end effector extending distally from the shaft, and a first actuator coupled to the handle and secured to a first wire. The first wire extends through the shaft, and the first actuator is configured to pivot relative to the shaft to pull the first wire proximally and to deflect the end effector relative to the shaft.

19 Claims, 6 Drawing Sheets

(52) U.S. Cl.
CPC .......... *A61B 17/29* (2013.01); *A61B 17/2909* (2013.01); *A61B 2017/291* (2013.01)

(56) References Cited

U.S. PATENT DOCUMENTS

| | | | | |
|---|---|---|---|---|
| 5,618,294 | A * | 4/1997 | Aust | A61B 1/0052 606/174 |
| 5,899,914 | A * | 5/1999 | Zirps | A61B 17/1608 606/174 |
| 5,938,678 | A * | 8/1999 | Zirps | A61B 17/29 606/174 |
| 5,967,997 | A * | 10/1999 | Turturro | A61B 10/06 600/567 |
| 6,077,287 | A * | 6/2000 | Taylor | A61B 17/1608 606/205 |
| 6,436,122 | B1 * | 8/2002 | Frank | A61B 17/2909 606/208 |
| 6,443,943 | B1 * | 9/2002 | Ouchi | A61B 17/2909 606/1 |
| 6,569,105 | B1 * | 5/2003 | Kortenbach | A61B 10/06 606/167 |
| 6,666,854 | B1 | 12/2003 | Lange | |
| 7,052,489 | B2 * | 5/2006 | Griego | A61B 17/29 606/1 |
| 7,927,327 | B2 * | 4/2011 | Lu | A61B 17/221 606/1 |
| 8,579,176 | B2 | 11/2013 | Smith et al. | |
| 8,795,325 | B2 * | 8/2014 | Taylor | A61B 17/2909 606/205 |
| 8,852,228 | B2 * | 10/2014 | Nau, Jr. | A61B 18/1445 606/50 |
| 9,005,238 | B2 * | 4/2015 | DeSantis | A61B 17/2909 606/205 |
| 9,138,250 | B2 * | 9/2015 | Lu | A61B 17/32056 |
| 9,510,846 | B2 | 12/2016 | Sholev et al. | |
| 2007/0225562 | A1 | 9/2007 | Spivey et al. | |
| 2007/0225754 | A1 * | 9/2007 | Measamer | A61B 17/2909 606/205 |
| 2007/0250110 | A1 * | 10/2007 | Lu | A61B 17/32056 606/205 |
| 2007/0282167 | A1 * | 12/2007 | Barenboym | A61B 1/0052 600/131 |
| 2008/0294191 | A1 * | 11/2008 | Lee | A61B 17/29 606/1 |
| 2009/0054734 | A1 * | 2/2009 | DeSantis | A61B 17/2909 600/153 |
| 2010/0076260 | A1 | 3/2010 | Taylor et al. | |
| 2011/0184459 | A1 | 7/2011 | Malkowski et al. | |
| 2012/0109186 | A1 * | 5/2012 | Parrott | A61B 17/29 606/206 |
| 2012/0253131 | A1 * | 10/2012 | Malkowski | A61B 34/30 606/1 |
| 2012/0277762 | A1 * | 11/2012 | Lathrop | A61B 34/70 606/130 |
| 2014/0088355 | A1 | 3/2014 | Schaeffer | |
| 2014/0251042 | A1 * | 9/2014 | Asselin | F16H 21/40 74/89 |
| 2015/0305797 | A1 * | 10/2015 | Hassoun | A61B 17/2909 606/208 |
| 2016/0228113 | A1 | 8/2016 | Weitzner et al. | |
| 2017/0007224 | A1 * | 1/2017 | Sholev | A61B 17/00234 |
| 2017/0095922 | A1 | 4/2017 | Licht et al. | |
| 2019/0029498 | A1 * | 1/2019 | Mankowski | A61B 1/0057 |
| 2020/0054194 | A1 * | 2/2020 | Melsheimer | A61B 1/015 |
| 2021/0353131 | A1 * | 11/2021 | Saito | A61B 1/0057 |

* cited by examiner

MEDICAL ARTICULATION DEVICES AND METHODS OF USING THE SAME

CROSS-REFERENCE TO RELATED APPLICATIONS

This application claims the benefit of priority of U.S. Provisional Patent Application No. 63/081,795, filed Sep. 22, 2020, the entirety of which is incorporated herein by reference.

TECHNICAL FIELD

Various aspects of the disclosure relate generally to medical articulation systems, devices, and related methods. Examples of the disclosure relate to systems, devices, and related methods for articulating a medical tool relative to a subject, among other aspects.

BACKGROUND

Endoscopic and surgical procedures of the gastrointestinal (GI) tract include, for example, submucosal dissection, colonic resection, bariatric surgery, esophagectomy, gastric bypass, and sleeve gastrectomy, among others. These procedures may involve lifting and/or removing tissue from the body of a patient. Accessory devices for performing such procedures may include complex interfaces for operating said device. Further, the interfaces may provide limited articulating capabilities for maneuvering the device within the patient, thereby requiring use of additional devices or multiple hands to manipulate said device.

SUMMARY

Aspects of the disclosure relate to, among other things, systems, devices, and methods for treating a target treatment site using an articulating device providing enhanced degree of maneuverability, among other aspects. Each of the aspects disclosed herein may include one or more of the features described in connection with any of the other disclosed aspects.

According to an example, a medical device includes a handle, a shaft extending distally from the handle, an end effector extending distally from the shaft, and a first actuator coupled to the handle and secured to a first wire. The first wire extends through the shaft, and the first actuator is configured to pivot relative to the shaft to pull the first wire proximally and to deflect the end effector relative to the shaft.

Any of the medical devices described herein may include any of the following features. The first actuator is pivotably coupled to the handle about a pivot joint positioned at a proximal end of the handle. The first actuator is configured to deflect the end effector relative to the shaft in response to pivoting about the pivot joint. The first actuator and the handle are pivotable relative to the shaft about a pivot joint at a distal end of the handle. The first actuator is configured to deflect the end effector relative to the shaft in response to pivoting the handle about the pivot joint. The first actuator includes a housing having a first channel that is angled relative to a longitudinal axis of the handle. The first channel is configured to receive a proximal portion of the first wire such that the first wire is positioned within the housing body at the angle relative to the longitudinal axis. The housing includes a distal opening aligned with the first channel. The distal opening has a height that permits vertical movement of the first wire relative to the distal opening. The first wire extends distally from the housing and exits the first channel through the distal opening. The handle includes a second channel and a proximal opening. The second channel is aligned with the first channel and receives the first wire through the proximal opening. The proximal opening includes a height that permits vertical movement of the first wire relative to the proximal opening. The proximal opening includes a tapered configuration such that a size of the proximal opening decreases from a proximal end to a distal end of the proximal opening. The first actuator is configured to translate the first wire through the second channel in response to pivoting the first actuator relative to the handle. Further including a second actuator coupled to the handle and secured to a second wire. The second wire extends through the shaft, and is coupled to the end effector. The second actuator is configured to translate relative to the handle to pull the second wire proximally to actuate the end effector. Further including a housing positioned between the handle and the shaft. The handle is movably coupled to a proximal end of the housing, and the shaft extends distally from a distal end of the housing. The handle and the first actuator are configured to pivot relative to the housing. The proximal end of the housing includes a pin, and a distal end of the handle includes an opening that is configured to receive the pin. The pin and the opening define a pivot joint between the handle and the housing. The proximal end of the housing includes a cavity with one or more ramps. The cavity is configured to receive a joint of the handle, and the one or more ramps are configured to guide movement of the joint within the cavity.

According to another example, a medical device includes a handle having a first movable actuator and a second movable actuator. The medical device includes a shaft extending distally from the handle and having an end effector at a distal end of the shaft. The medical device includes an articulation wire disposed within the shaft, and coupled to the first movable actuator and a distal portion of the medical device. The medical device includes an actuation wire disposed within the shaft, and coupled to the second movable actuator and the end effector. The first movable actuator is configured to deflect the end effector relative to the shaft in response to translating the articulation wire proximally when the first movable actuator pivots relative to the shaft. The second movable actuator is configured to actuate the end effector in response to translating the actuation wire proximally when the second movable actuator translates relative to other portions of the handle.

Any of the medical devices described herein may include any of the following features. The first movable actuator is configured to deflect the end effector in a first direction in response to the first movable actuator pivoting in the first direction. Further including a housing positioned between the handle and the shaft. The handle is movably coupled to a proximal end of the housing, and the shaft extends distally from a distal end of the housing. The proximal end of the housing includes a pin, and a distal end of the handle includes an opening that is configured to receive the pin, with the pin and the opening defining a pivot joint between the handle and the housing. The handle, the first movable actuator, and the second movable actuator are configured to pivot relative to the housing about the pivot joint. The proximal end of the housing includes a cavity with one or more ramps. The cavity is configured to receive a joint of the handle and the one or more ramps are configured to guide movement of the joint within the cavity.

According to a further example, a medical device includes a handle, a shaft extending distally from the handle, and an end effector at a distal end of the shaft. The medical device includes a first actuator including a first wire disposed within the shaft. The first actuator is pivotable relative to the shaft. The medical device includes a second actuator including a second wire disposed within the shaft. The second actuator is slidable relative to the handle. The first actuator is configured to retract the first wire proximally relative to the shaft to deflect the end effector. The second actuator is configured to retract the second wire proximally relative to the shaft to move the end effector from an open configuration to a closed configuration.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

In ESD, an object in the GI tract is targeted for removal, such as, for example, a tumor. A medical device capable of removing the target object is received in a medical instrument (e.g., an endoscope) that is endoscopically placed through the GI tract and at the target treatment site. An ancillary device may be placed endoscopically at the target treatment site for manipulating tissue surrounding the target object. Ancillary devices and systems suited for ESD are limited, however. Examples of this disclosure may be used in endoscopic procedures, such as ESD. The disclosure, however, is not limited to ESD procedures, and instead can be used in any suitable medical procedure.

Examples of the disclosure include systems, devices, and methods for manipulating materials and/or objects (e.g., tissue) at a target treatment site within a subject (e.g., patient) with enhanced degree of maneuverability. In examples, ESD includes endoluminal placement of an end effector, e.g., a jaw assembly or other like tool, into the target treatment site. Placement of the end effector may be via a catheter, a scope (endoscope, bronchoscope, colonoscope, etc.), a tube, or a sheath inserted into the GI tract via a natural orifice. The orifice can be, for example, the nose, mouth, or anus, and the placement can be in any portion of the GI tract, including the esophagus, stomach, duodenum, large intestine, or small intestine. Placement also can be in other organs or other bodily spaces reachable via the GI tract, other body lumens, or opening in the body.

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). Various examples described herein include single-use or disposable medical devices.

Figure 1:
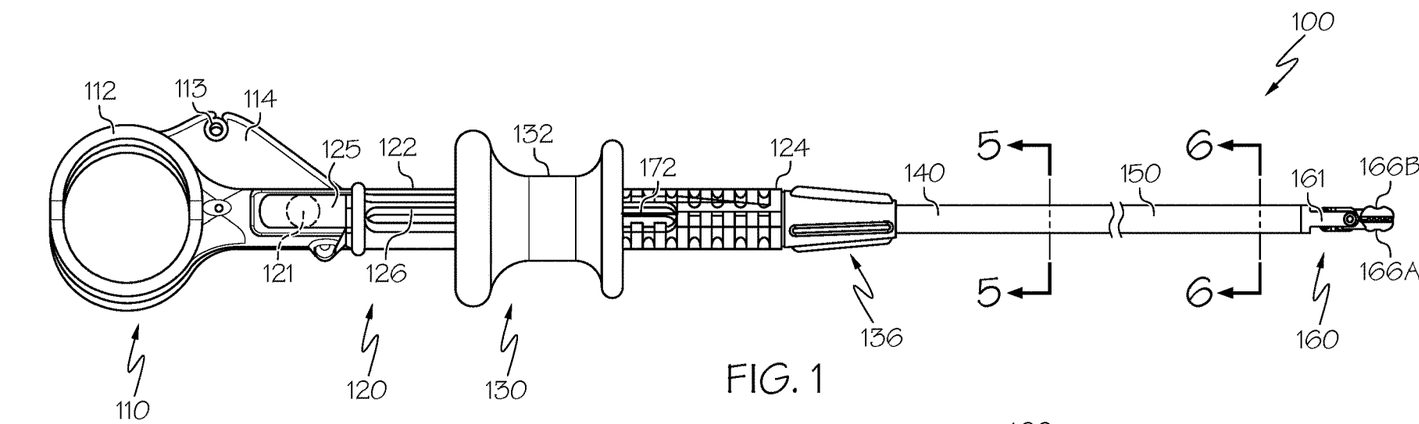
FIG. 1 is a side view of an exemplary medical device including a pair of actuators, a handle, and an effector, according to aspects of this disclosure.

FIG. 1 shows an exemplary medical device 100 in accordance with an example of this disclosure. Medical device 100 may include a handle 120 having a longitudinal length defined between a proximal end 122 and a distal end 124. Handle 120 may further include a slot 126 formed through a cylindrical body of handle 120. Slot 126 may extend along an intermediate portion of handle 120 between proximal end 122 and distal end 124. As described in further detail herein, handle 120 may include one or more lumens extending between proximal end 122 and distal end 124, and at least one of the one or more lumens may be aligned with and/or extend into slot 126 (see FIG. 4). Handle 120 may further include a proximal extension 125 extending proximally from proximal end 122.

Medical device 100 may further include a first actuator 110 movably coupled to handle 120 at proximal end 122, and a second actuator 130 movably coupled to handle 120 between proximal end 122 and distal end 124. First actuator 110 may be positioned proximally of proximal end 122 and engaged to proximal extension 125. First actuator 110 may include a grasping feature 112 that is configured to be manually grasped by a user of medical device 100. In the example, grasping feature 112 may include a ring positioned, sized, and/or shaped to receive a digit of a user therethrough (e.g., a thumb, etc.). As described further herein, first actuator 110 may be configured to move (e.g., pivot, rotate, etc.) relative to handle 120.

Still referring to FIG. 1, second actuator 130 may include a spool 132 defining a body of second actuator 130, with spool 132 having an ergonomic configuration that is configured to be manually grasped by a user of medical device 100. In the example, spool 132 may include one or more curvatures and/or surfaces providing an intuitive interface for controlling medical device 100. For example, spool 132 may be sized and shaped to receive one or more fingers of a user thereon (e.g., a forefinger, a middle finger, etc.). Second actuator 130 further defines a channel extending through spool 132, the channel being configured to receive handle 120 therethrough. Thus, second actuator 130 may be disposed about an exterior circumference of handle 120 and positioned over slot 126.

Slot 126 may be configured to receive at least a portion of second actuator 130 therein. Although not shown, it should be understood that second actuator 130 may include one or more protrusions extending radially inward from an interior surface of spool 132. The one or more protrusions may be received within slot 126 and, as described in further detail herein, the protrusions may be configured to engage an actuation wire (e.g., a first wire) disposed within slot 126. In this instance, slot 126 may define a travel path and/or stroke length of second actuator 130 relative to handle 120. Stated differently, a longitudinal movement of second actuator 130 may be defined by a longitudinal length of slot 126. It should be appreciated that at least a portion of second actuator 130 (e.g., spool 132) may be configured to move (e.g., translate, etc.) over handle 120 while another portion of second actuator 130 (e.g., protrusions) may be configured to move (e.g., translate, etc.) within slot 126.

Still referring to FIG. 1, handle 120 may include one or more surface features (e.g., ridges, ribs, protrusions, etc.) along an exterior surface, such as, for example, adjacent to distal end 124. The surface feature(s) may provide increased control of handle 120. Handle 120 may further include an end cap 136 at distal end 124. End cap 136 may include one or more surface features (e.g., ridges, ribs, protrusions, etc.) disposed along an exterior surface for facilitating a manual manipulation of end cap 136. For example, end cap 136 may be selectively coupled to distal end 124 in response to a rotation of end cap 136 relative to handle 120. In some embodiments, end cap 136 may be secured to distal end 124 via an adhesive, a heat shrink, a snap-fit connection, a threaded coupling, a welding, and the like. It should be appreciated that end cap 136 may be securely fixed to handle 120 (i.e. irremovable) upon attachment to distal end 136. End cap 136 may be formed of plastic, acrylic, metal, and various other suitable materials.

Medical device 100 may further include a shaft 140 extending distally from handle 120, and an articulation joint 150 extending distally from shaft 140. End cap 136 may be configured to attach shaft 140 to distal end 124 of handle 120 by, for example, an adhesive, a heat shrink, a snap-fit connection, a threaded coupling, a crimped sleeve, and the like. In the example, shaft 140 may include a longitudinal length defined between a proximal end of shaft 140 (connected to distal end 124 and/or end cap 136) and a distal end of shaft 140 (connected to a proximal end of articulation joint 150). As described in further detail herein, each of shaft 140 and articulation joint 150 may include a plurality of layers that may vary relative to one another. Medical device 100 may further include an end effector 160 coupled to a distal end of articulation joint 150.

Figure 2:
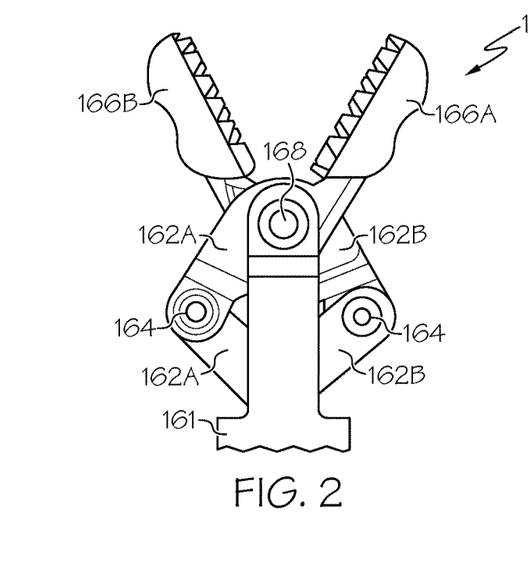
FIG. 2 is a side view of the end effector of the medical device of FIG. 1, according to aspects of this disclosure.

Referring now to FIG. 2, end effector 160 may include a jaw assembly having a clevis 161, a plurality of first links 162A, a plurality of second links 162B, a first jaw 166A, and a second jaw 166B. Clevis 161 may be secured to a distal end of articulation joint 150. A proximalmost first link 162A and a proximalmost second link 162B may be positioned adjacent to clevis 161. The distalmost first link 162A may be pivotably coupled to the proximalmost first link 162A at a pin 164, and the distalmost second link 162B may be pivotably coupled to the proximalmost second link 162B at another pin 164. In the embodiment, distalmost first link 162A may be integral with first jaw 166A, and distalmost second link 162B may be integral with second jaw 166B. First jaw 166A and second jaw 166B may be movably coupled to clevis 151 about a pin 168. Each jaw 166A, 166B may include a plurality of teeth positioned along an interior surface of the jaw 166A, 166B.

As described in further detail herein, the plurality of first links 162A and the plurality of second links 162B may be coupled to actuation wire (e.g., the first wire) that is configured to transition jaws 166A, 166B between an actuated state (see FIG. 1) and an unactuated state (see FIG. 2). It should be understood that end effector 160 may include various suitable configurations, including, but not limited to, one or more clamps, shears, forceps, scissors, suturing devices, lighting devices, imaging systems, grasper assemblies, and various other suitable tools and/or devices. Accordingly, end effector 160 shown and described herein is merely exemplary such that medical device 100 may include various other end effectors without departing from a scope of this disclosure.

Figure 3:
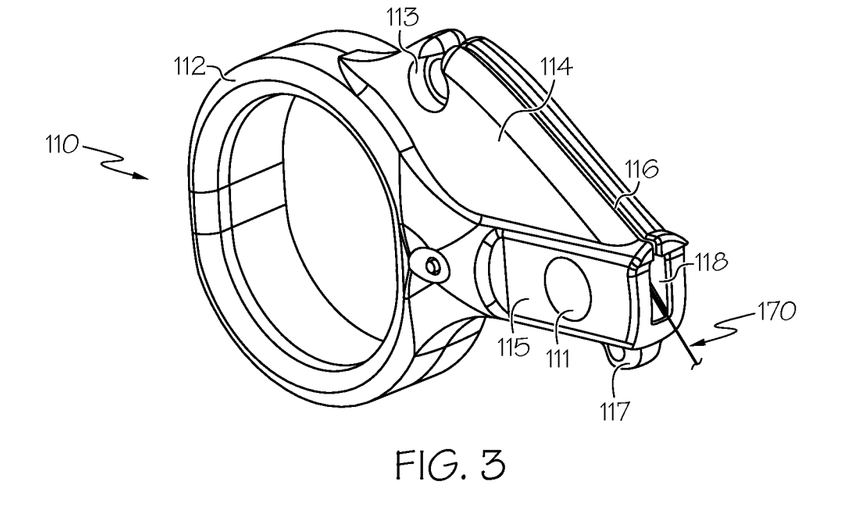
FIG. 3 is a perspective view of one of the pair of actuators of the medical device of FIG. 1, according to aspects of this disclosure.

Referring now to FIG. 3, first actuator 110 is depicted in a decoupled state from handle 120. First actuator 110 may include grasping feature 112 at a proximal end of first actuator 110 and a distal extension 115 at a distal end of first actuator 110. Distal extension 115 may include opposing sidewalls, each defining a planar surface that is configured to engage proximal extension 125 when first actuator 110 is coupled to handle 120. First actuator 110 may further include a pair of pin openings 111, with each pin opening 111 located on each of the opposing sidewalls of distal extension 115. Each pin opening 111 may be sized and shaped to receive a corresponding pin 121 of handle 120 (see FIG. 4) to couple first actuator 110 to handle 120. The pair of pin openings 111 may collectively define a hinge and/or pivot point between first actuator 110 and handle 120 when receiving the pair of pins 121 of handle 120.

First actuator 110 may further include a wire housing 114 positioned along a top wall of first actuator 110. In some embodiments, wire housing 114 may be selectively attached to first actuator 110, while in other embodiments wire housing 114 may be integrally formed with first actuator 110. It should be appreciated that wire housing 114 may be located along various other walls and/or surfaces of first actuator 110 than those shown and described herein. Wire housing 114 may include a channel 116 extending along a longitudinal length of wire housing 114 and formed on a top surface of wire housing 114.

Still referring to FIG. 3, channel 116 may define an angled surface (e.g., relative to a longitudinal length of first actuator 110 and/or handle 120) defined between a proximal attachment point 113 and a distal opening 118. It should be appreciated that a length, a width, and/or an angle of channel 116 or wire housing 114 may vary relative to the example shown and described herein. As described further herein, a length, a width, and/or an angle of channel 116 may at least partially define a degree of articulation of articulation joint 150, and a corresponding deflection of end effector 160. An articulation of articulation joint 150, and a deflection of end effector 160, may be further based on a degree of movement of first actuation 110 relative to handle 120. Wire housing 114 may be configured to receive an articulation wire 170 (e.g., a second wire) within channel 116. Stated differently, channel 116 may be sized and shaped to receive articulation wire 170.

A proximal end of articulation wire 170 may be fixed to wire housing 114 at the proximal attachment point 113 by various suitable mechanisms, including, for example, an adhesive, a fastener, welding, crimping, etc. In some embodiments, the proximal attachment point 113 may include a bearing received within an opening of wire housing 114. In this instance, the proximal end of articulation wire 170 may be fixed to wire housing 114 at the bearing (e.g., the proximal attachment point 113). Articulation wire 170 may extend distally from wire housing 114 via distal opening 118. Distal opening 118 may be sized and/or shaped to facilitate movement of articulation wire 170. In other words, distal opening 118 may have a profile that is greater than a diameter of articulation wire 170 to allow articulation wire 170 to move (e.g., longitudinally, laterally, etc.) relative to distal opening 118. In the example, distal opening 118 may include a height that is greater than a width of distal opening 118 to facilitate vertical (e.g., upward and downward) movement of articulation wire 170 through distal opening 118.

As described further herein, first actuator 110 may be configured to move (e.g., translate) articulation wire 170 relative to distal opening 118 in response to first actuator 110 moving (e.g., pivoting) relative to handle 120 about the pivot point at pin opening 111. In some embodiments, movement of first actuator 110 may be limited to one direction (e.g., upward, downward, etc.) relative to handle 120, while in other embodiments first actuator 110 may be movable in two or more directions.

Still referring to FIG. 3, first actuator 110 may further include a protrusion 117 extending outwardly from a bottom wall of first actuator 110 and adjacent to a distal end of first actuator 110. Protrusion 117 may be configured to limit movement of first actuator 110 relative to handle 120 (e.g., in a downward direction). As described in detail herein, protrusion 117 may abut against proximal end 122 in response to first actuator 110 moving (e.g., pivoting) relative to handle 120. Accordingly, a size, a shape, and/or a position of protrusion 117 relative to a distal end of first actuator 110, and proximal end 122 of handle 120, may collectively define an extent of movement of first actuator 110 relative to handle 120, and a corresponding movement of articulation wire 170 relative to distal opening 118. In other embodiments, first actuator 110 may include one or more features on a top wall (e.g., a protrusion) to further limit movement of first actuator 110 relative to handle 120 in an upward direction.

Figure 4:
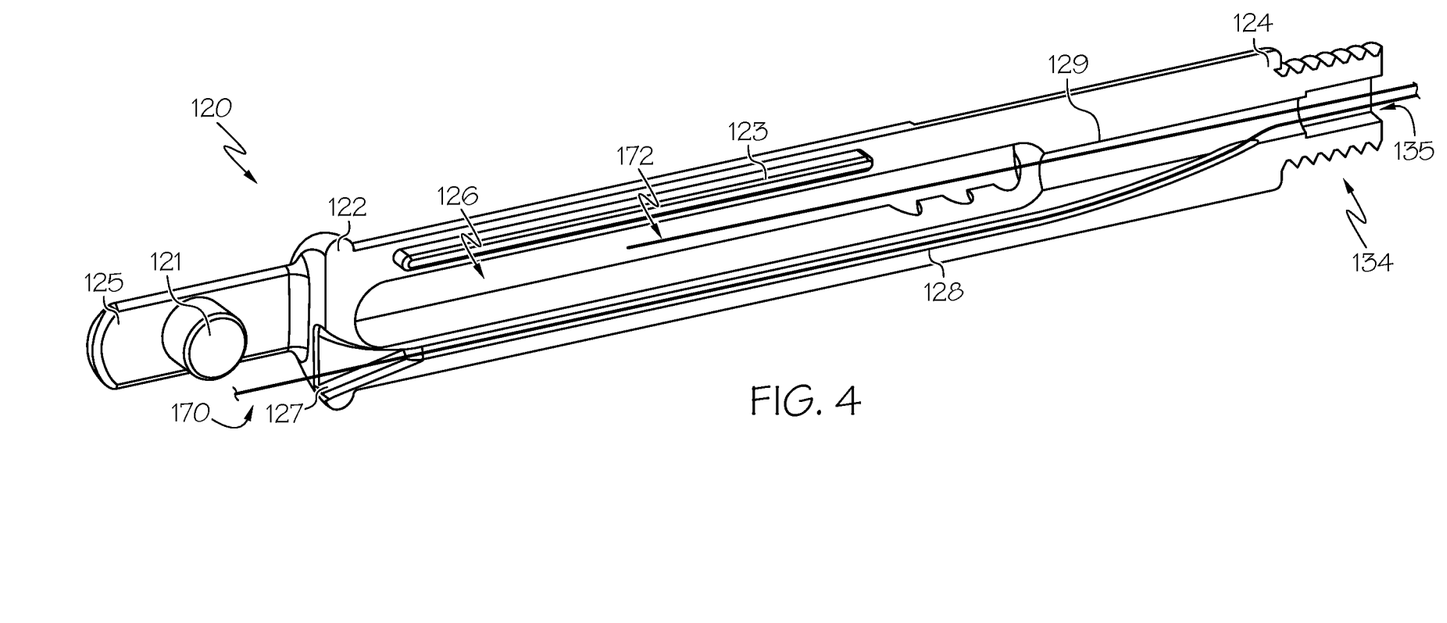
FIG. 4 is a partial perspective view of the handle of the medical device of FIG. 1, according to aspects of this disclosure.

Referring now to FIG. 4, handle 120 is partially depicted in a decoupled state from first actuator 110 and end cap 136. In the example, a body of handle 120 may include a pair of corresponding halves that are configured to mate with one another when assembled together. FIG. 4 shows one of the corresponding halves of handle 120 including pin 121 extending radially inward from proximal extension 125 and a mating feature 123 extending radially inward from an interior surface of handle 120. Mating feature 123 may be positioned between proximal end 122 and distal end 124. Mating feature 123 may be configured to couple the pair of corresponding halves of handle 120 to one another. Mating feature 123 may include any suitable mechanism for attaching a pair of halves of the body of handle 120 together. In the example, mating feature 123 may include a protrusion and the other corresponding half of handle 120 may include a recess configured to receive the protrusion.

Handle 120 may include a distal extension 134 extending distally from distal end 124. Distal extension 134 may include a threaded exterior that is configured to mate with a corresponding threaded lumen of end cap 134 to couple handle 120 to end cap 134. Handle 120 may further include a first lumen 128 and a second lumen 129 formed along an interior surface of handle 120. First lumen 128 may be defined between proximal end 122 and distal extension 134. In the example, first lumen 128 includes a proximal opening 127 positioned adjacent to proximal end 122. Proximal opening 127 may be aligned with distal opening 118 when handle 120 is coupled to first actuator 110. Accordingly, handle 120 may be configured to receive articulation wire 170 within first lumen 128 and from first actuator 110 via proximal opening 127.

Still referring to FIG. 4, proximal opening 127 may be sized and/or shaped to have a tapered profile to facilitate movement of articulation wire 170. Stated differently, proximal opening 127 may include an expanded configuration at an interface of proximal opening 127 at proximal end 122. Proximal opening 127 may include a gradual taper to a narrowed configuration that is sized substantially similar to a diameter of first lumen 128. The expanded configuration of proximal opening 127 may provide enhanced space, and more particularly a vertical clearance, for articulation wire 170 to move when first actuator 110 moves (e.g., pivots) relative to handle 120. In the example, proximal opening 127 may include a height that is greater than a width of proximal opening 127 to facilitate vertical (e.g., upward and downward) movement of articulation wire 170 through proximal opening 127.

Second lumen 129 may be defined between a distal end of slot 126 and distal extension 134. In the example, second lumen 129 may include an opening into slot 126. Second lumen 129 may be configured to receive an actuation wire 172 from slot 126. Accordingly, it should be understood that at least a proximal portion of actuation wire 172 may be received within slot 126. A proximal end of actuation wire 172 may be coupled to second actuator 130 (see FIG. 1) such that movement of second actuator 130 relative to handle 120 may provide movement (e.g., translation) of actuation wire 172 relative to slot 126 and through second lumen 129. In some embodiments, second actuator 130 may include a sleeve (not shown) disposed within spool 132, and the proximal end of actuation wire 172 may be crimped to the sleeve to secure actuation wire 172 to second actuator 130.

Still referring to FIG. 4, first lumen 128 and second lumen 129 may be interconnected with one another at an intermediate point along a longitudinal length of second lumen 129. For example, a distal end of first lumen 128 may extend into second lumen 129 at distal end 124. Accordingly, articulation wire 170 may be received in second lumen 129. Second lumen 129 may terminate at a distal opening 135 of distal extension 134, which may be aligned with one or more lumens of shaft 140 and articulation joint 150 (see FIGS. 5-6).

Figure 5:
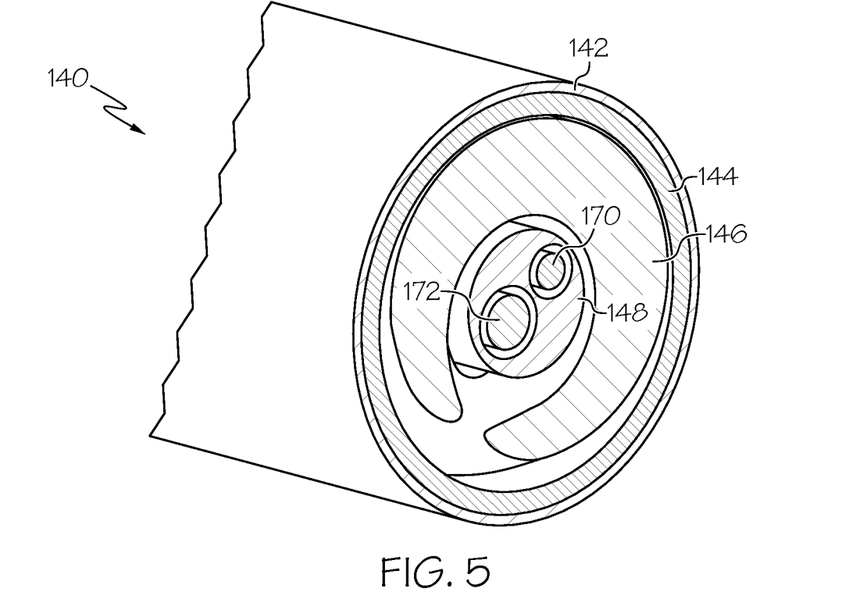
FIG. 5 is a cross-sectional perspective view of a shaft of the medical device of FIG. 1, according to aspects of this disclosure.

Referring now to FIG. 5, shaft 140 is depicted with a plurality of layers. In the example, shaft 140 may include an outer layer 142, a first inner layer 144, a second inner layer 146, and a third inner layer 148. Outer layer 142 may be disposed about first inner layer 144, and may be configured to insulate first inner layer 144, such as, for example, from a tool (e.g., cautery knife) positioned adjacent to medical device 100. In some examples, outer layer 142 may be formed of an insulating material, such as, for example, reflow including Pebax® resin. Outer layer 142 may be further formed of a material having a predefined hardness ranging from about 10 D (durometer) to about 100 D, and more particularly 30 D to 75 D. In other embodiments, outer layer 142 may be omitted entirely. First inner layer 144 may be disposed about second inner layer 146, and may include a braid formed of a plurality of wires (e.g., flat, round, etc.) braided to one another. In some examples, first inner layer 144 may include a plurality of wires ranging from about 10 wires to about 100 wires, and more particularly 16 to 32 wires. First inner layer 144 may be configured to increase a torque and/or stiffness of shaft 140. In other embodiments, first inner layer 144 may be omitted entirely.

Second inner layer 146 may be disposed about third inner layer 148, and may include a coil that is wound (e.g., clockwise, counter clockwise, etc.) about third inner layer 148. Second inner layer 146 may be configured to provide a rigidity to shaft 140.

Third inner layer 148 may be formed of polytetrafluoroethylene (PTFE) and include a pair of lumens for receiving each of articulation wire 170 and actuation wire 172. In the example, the lumens of third inner layer 148 may have similar and/or different diameters relative to one another. Third inner layer 148 may include a diameter ranging from about 0.5 millimeters to about 1.0 millimeters, and particularly 0.8 millimeters. An articulation lumen of third inner layer 148 for receiving articulation wire 170 may include a diameter ranging from about 0.2 millimeters to about 0.8 millimeters, and particularly 0.4 millimeters. An actuation lumen of third inner layer 148 for receiving actuation wire 172 may include a diameter ranging from about 0.1 millimeters to about 0.7 millimeters, and particularly 0.3 millimeters. In other embodiments, third inner layer 148 may be omitted in lieu of a pair of sheaths each defining a lumen for receiving at least one of wires 170, 172.

Still referring to FIG. 5, articulation wire 170 and actuation wire 172 may be formed of various materials, including, for example, stainless steel, Nitinol, plastic, aluminum, etc. In some examples, articulation wire 170 and/or actuation wire 172 may be coated with PTFE and/or other suitable materials. Additionally, articulation wire 170 and/or actuation wire 172 may each include a single wire or may be a multi-strand wire assembly.

Figure 6:
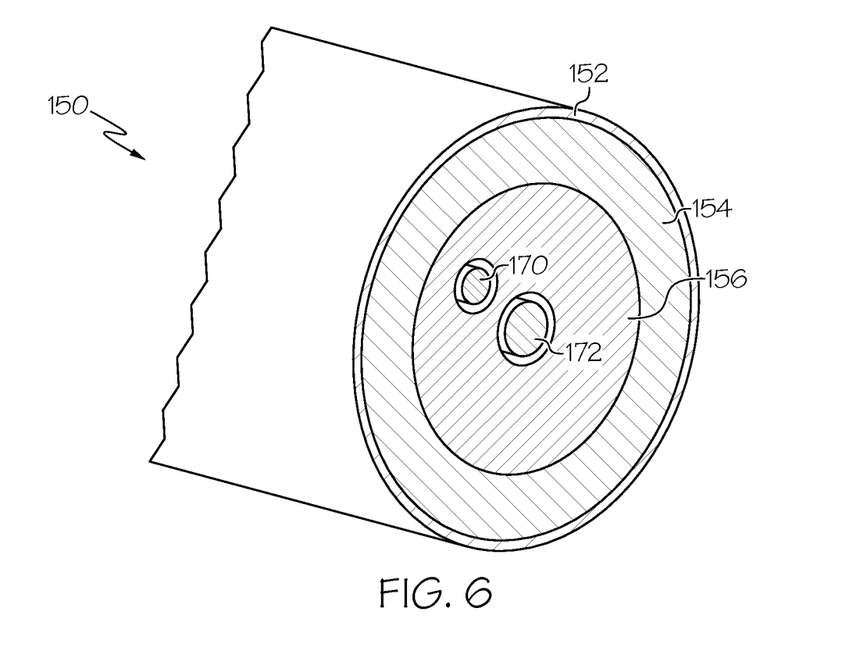
FIG. 6 is a cross-sectional perspective view of an articulation joint of the medical device of FIG. 1, according to aspects of this disclosure.

Referring now to FIG. 6, articulation joint 150 is depicted with a plurality of layers. In the example, articulation joint 150 may include an outer layer 152, a first inner layer 154, and a second inner layer 156. Outer layer 152 may be disposed about first inner layer 154, and may be configured to insulate first inner layer 154. For example, outer layer 152 may be formed of an insulating material, such as, for example, reflow including Pebax® resin. Outer layer 152 may be formed of a material having a predefined hardness that is relatively less than outer layer 142. For example, outer layer 152 may have a predefined hardness ranging from about 5 D to about 100 D, and more particularly 30 D to about 50 D. As described in detail herein, articulation joint 150 may be configured to bend relative to shaft 140 in response to an actuation of articulation wire 170.

First inner layer 154 may be disposed about second inner layer 156, and may include a braid formed of a plurality of wires (e.g., flat, round, etc.) braided to one another. First inner layer 154 may be substantially similar to first inner layer 144. For example, first inner layer 154 may include a plurality of wires ranging from about 10 wires to about 100 wires, and more particularly 16 to 32 wires. In other examples, first inner layer 154 may include fewer wires than first inner layer 144. First inner layer 154 may be configured to increase a torque and/or stiffness of articulation joint 150. In some embodiments, a braiding of first inner layer 154 may be angled, such as at an angle ranging from about 10 degrees to about 100 degrees, and more particularly 30 to 40 degrees.

Still referring to FIG. 6, second inner layer 156 may be formed of polytetrafluoroethylene (PTFE), and may include a pair of lumens for receiving each of articulation wire 170 and actuation wire 172. In the example, the lumens of second inner layer 156 may have similar and/or different diameters relative to one another. In other embodiments, second inner layer 156 may be omitted in lieu of a pair of sheaths each defining a lumen for receiving at least one of wires 170, 172. Second inner layer 156 may be formed of a material having a predefined hardness ranging from about 15 D to about 95 D, and more particularly 33 D to 50 D. Articulation wire 170 may extend distally from second inner layer 156 and may be attached to clevis 161. Articulation wire 170 may be secured to clevis 161 by an adhesive, welding, crimping, ultraviolet (UV) curing, etc. In other embodiments, articulation wire 170 may be attached to a distal end of articulation joint 150 in lieu of clevis 161. Actuation wire 172 may extend distally from second inner layer 156 and may be attached to the proximalmost first link 162A and the proximalmost second link 162B (see FIG. 2). Articulation wire 170 may be secured to links 162A, 162B by an adhesive, welding, crimping, ultraviolet (UV) curing, etc.

According to an exemplary method of using medical device 100, a medical instrument (e.g., an endoscope) may be initially navigated through the body of a subject to position a distal end of the medical instrument at a target treatment site. Medical device 100 may be received within the medical instrument, and end effector 160 may extend outwardly from the distal end of the medical instrument. In this instance, end effector 160 may be positioned within the subject and at the target treatment site while handle 120 is positioned external from the subject at a proximal end of the medical instrument. It should be appreciated that end effector 160 will be maintained in an actuated (closed) state during delivery through the medical instrument.

Figure 7A:
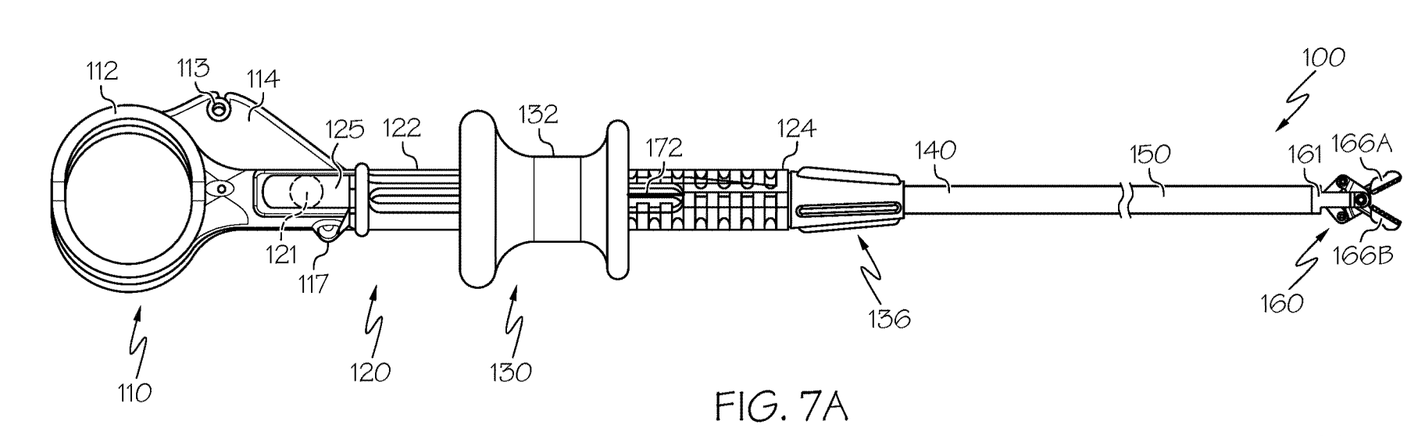
FIG. 7A is a side view of the medical device of FIG. 1, with the articulation joint in an unarticulated position and the end effector in an unactuated state, according to aspects of this disclosure.

Referring now to FIG. 7A, first actuator 110 may be positioned in a first configuration relative to handle 120 such that articulation joint 150 is maintained in an unarticulated state. Stated differently, first actuator 110 may be positioned in parallel alignment with handle 120 such that articulation wire 170 (connected to wire housing 114) is extended to a distalmost position within channel 116 (FIG. 3), first lumen 128 (FIG. 4), shaft 140, and articulation joint 150 (FIGS. 5-6). In this instance, articulation wire 170 does not apply a tensile force onto clevis 161, thereby maintaining articulation joint 150 in an unarticulated state and parallel to shaft 140 and/or handle 120.

Second actuator 130 may be positioned in a first configuration relative to handle 120 such that end effector 160 is maintained in an unactuated (open) state. Stated differently, second actuator 130 may be positioned proximate to distal end 124 (relative to proximal end 122) and adjacent to a distal end of slot 126. Accordingly, actuation wire 172 (connected to spool 132) is extended to a distalmost position within slot 126, second lumen 129 (FIG. 4), shaft 140, and articulation joint 150 (FIGS. 5-6). In this instance, actuation wire 172 does not apply a tensile force onto the proximalmost first link 162A and the proximalmost second link 162B, thereby maintaining jaws 166A, 166B in an unactuated state.

Figure 7B:
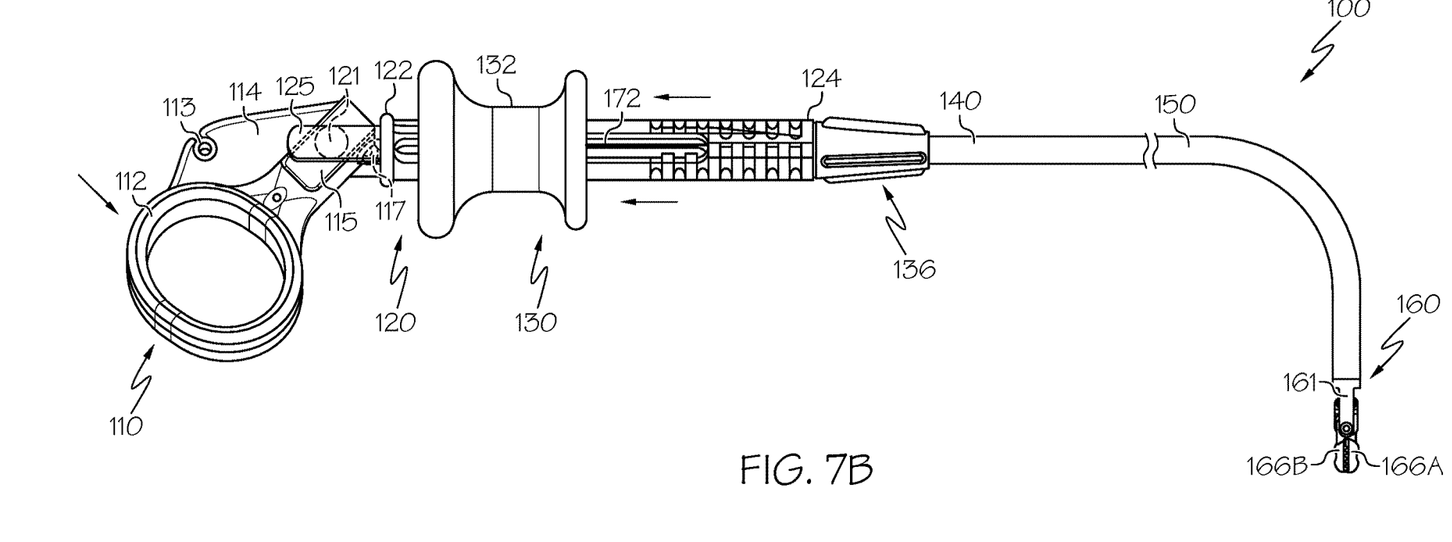
FIG. 7B is a side view of the medical device of FIG. 1, with the articulation joint in an articulated position and the end effector in an actuated state, according to aspects of this disclosure.

Referring now to FIG. 7B, first actuator 110 may be actuated to position end effector 160 at a position adjacent to a target object (e.g., tissue) within the target treatment site. For example, a user of medical device 100 may move first actuator 110 relative to handle 120 by pivoting first actuator 110 about the pivot point defined by pin openings 111 and pins 121. First actuator 110 may pivot relative to handle 120 in response to applying a force (e.g., downward, upward, etc.) at grasping feature 112. In this instance, wire housing 114 may move with grasping feature 112 in a first direction relative to handle 120. With articulation wire 170 secured to wire housing 114, first actuator 110 may be configured to move articulation wire 170 relative to handle 120, shaft 140, and articulation joint 150.

First actuator 110 may pull articulation wire 170 proximally to apply a proximal (pulling) force onto clevis 161, thereby causing articulation joint 150 to bend. In this instance, end effector 160 may be deflected in the first direction, i.e. the same direction of movement as first actuator 110 relative to handle 120. It should be understood that articulation wire 170 may be attached to a bottom (off-centered) portion of clevis 161 (see FIGS. 7A-7B) to allow articulation joint 150 to bend when first actuator 110 is moved downward. A user of medical device 100 may selectively adjust a degree of articulation of articulation joint 150, and the corresponding extent of deflection of end effector 160, in response to a degree of movement of first actuator 110 relative to handle 120. Further, first actuator 110 and handle 120 may be rotated to move end effector 160 relative to the target treatment site to facilitate further movement of medical device 100 toward the target object.

Still referring to FIG. 7B, second actuator 130 may be actuated to transition end effector 160 from an unactuated state (FIG. 7A) to an actuated state. For example, a user of medical device 100 may move second actuator 130 relative to handle 120 by sliding spool 132 through slot 126. Second actuator 130 may translate over handle 120 in response to applying a force (e.g., proximal, distal, etc.) on spool 132. In this instance, actuation wire 172 may translate with spool 132 relative to handle 120. Second actuator 130 may pull actuation wire 172 proximally to apply a proximal (pulling) force onto the plurality of links 162A, 162B, thereby causing jaws 166A, 166B to engage one another. In this instance, end effector 160 clamps against a target object (e.g., tissue) positioned between jaws 166A, 166B. A user of medical device 100 may selectively adjust a degree of engagement between jaws 166A, 166B in response to an extent of translation of spool 132.

Figure 8A:
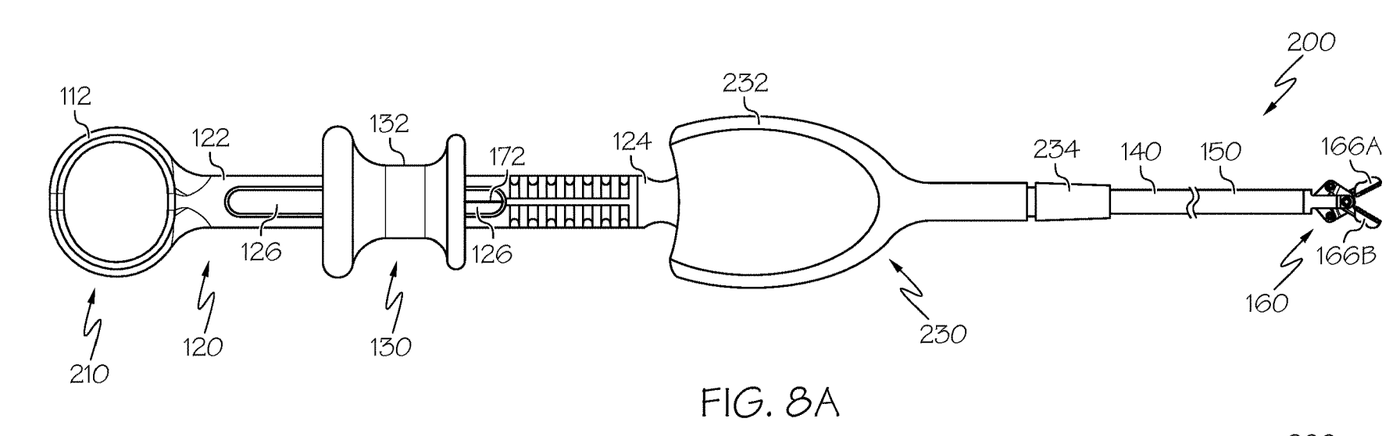
FIG. 8A is a side view of another exemplary medical device, with an articulation joint in an unarticulated position and an end effector in an unactuated state, according to aspects of this disclosure.
Figure 8B:
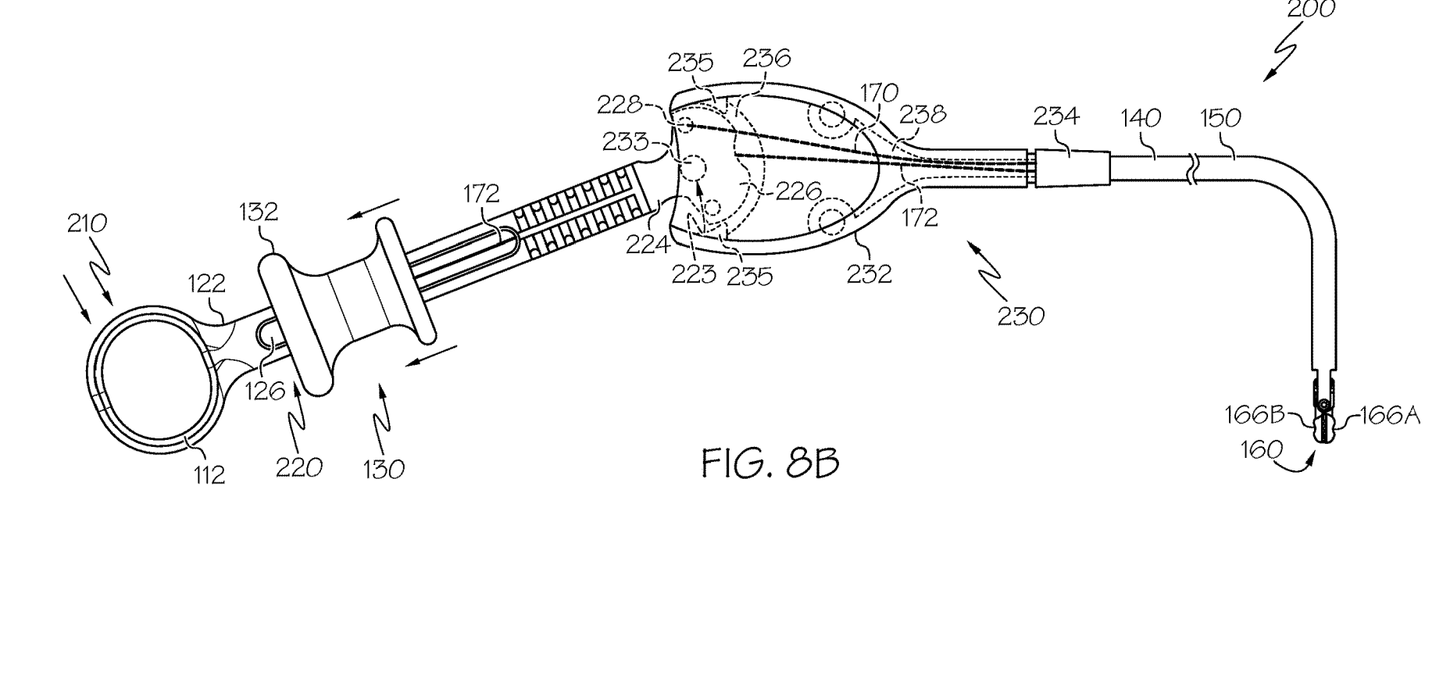
FIG. 8B is a side view of the medical device of FIG. 8A, with the articulation joint in an articulated position and an end effector in an actuated state; according to aspects of this disclosure.

Referring now to FIGS. 8A-8B, another exemplary medical device 200 is depicted according to an example of the disclosure. Except as otherwise described herein, medical device 200 may be configured and operable similar to medical device 100. Accordingly, like reference numerals are used to identify like components. For example, medical device 200 may include handle 120 having a longitudinal length defined between proximal end 122 and distal end 124. Medical device 200 may further include shaft 140 extending distally from handle 120, articulation joint 150 extending distally from shaft 140, and end effector 160 coupled to a distal end of articulation joint 150.

Medical device 200 may include a first actuator 210 at proximal end 122, and first actuator 210 may include grasping feature 112. First actuator 210 may be fixed relative to proximal end 122 such that first actuator 210 is immovable relative to handle 120. As described in further detail below, first actuator 210 may be configured to move (e.g., pivot) handle 120 relative to shaft 140 in response to applying a force onto grasping feature 112. Medical device 200 may further include a wire housing 230 movably coupled to, and positioned between, handle 120 and shaft 140. For example, wire housing 230 may include a proximal body 232 coupled to handle 120 and a distal body 234 coupled to shaft 140. Proximal body 232 may have a greater cross-sectional profile than distal body 234, and wire housing 230 may define a hinge and/or pivot point between handle 120 and shaft 140.

Referring specifically to FIG. 8B, proximal body 232 may define a cavity 236 having a semi-circular profile and including a pair of curved ramps 235 disposed therein. Cavity 236 may be sized and shaped to receive at least a portion of distal end 224, and cavity 236 may define a travel path of handle 120 relative to wire housing 230. In the example, handle 120 may include a joint 226 at distal end 224, and joint 226 may be disposed within cavity 236. The pair of curved ramps 235 may engage joint 226 and facilitate movement of joint 226 within cavity 236. Wire housing 230 may include a pin 233 disposed within cavity 236. Pin 233 may be configured to engage a pin opening 223 of joint 226, and handle 120 may be movably coupled to wire housing 230 at the connection between pin opening 223 and pin 233. It should be understood that an engagement between pin 233 and pin opening 223 may inhibit handle 120 from exiting wire housing 230.

Joint 226 may include one or more attachment points 228 for coupling a proximal end of articulation wire 170 to handle 120. As described in further detail herein, handle 120 may be configured to move articulation wire 170 in response to moving joint 226 within cavity 236. Actuation wire 172 may be secured to second actuator 130 and received within cavity 236 through joint 226. Wire housing 230 may further include a second cavity 238 positioned distal to cavity 236 and disposed between proximal body 232 and distal body 234. Second cavity 238 may have a narrowed configuration with a smaller cross-sectional profile than cavity 236. Wires 170, 172 may extend through second cavity 238 and into shaft 140 via distal body 234.

According to an exemplary method of using medical device 200, medical device 200 may be received within a medical instrument (e.g., an endoscope) that is positioned at a target treatment site in a manner similar to that described in detail above with respect to medical device 100. End effector 160 may be positioned within at the target treatment site while handle 120 is positioned external from the subject.

Referring now to FIG. 8A, handle 120 may be positioned in a first configuration relative to wire housing 230 such that articulation joint 150 is maintained in an unarticulated state. In this instance, handle 120 may be positioned in parallel alignment with wire housing 230 (e.g., a longitudinal axis of handle 120 may be aligned with a longitudinal axis of housing 230 and shaft 240), such that articulation wire 170 (connected to joint 226) is maintained in a central position within cavity 236 (FIG. 8B), first lumen 128 (FIG. 4), shaft 140, and articulation joint 150 (FIGS. 5-6). In this instance, articulation wire 170 does not apply a tensile force onto clevis 161, thereby maintaining articulation joint 150 in an unarticulated state and parallel to shaft 140 and/or handle 120.

Second actuator 130 may be positioned in a first configuration relative to handle 120 such that end effector 160 is maintained in an unactuated state. Accordingly, actuation wire 172 (connected to spool 132) is extended to a distalmost position within slot 126, second lumen 129 (FIG. 4), shaft 140, and articulation joint 150 (FIGS. 5-6). In this instance, actuation wire 172 does not apply a tensile force onto the proximalmost first link 162A and the proximalmost second link 162B, thereby maintaining jaws 166A, 166B in an unactuated state.

Referring now to FIG. 8B, first actuator 210 may be actuated to position end effector 160 at a position adjacent to a target object (e.g., tissue) within the target treatment site. For example, a user of medical device 200 may move first actuator 210 and handle 120 relative to wire housing 230 by pivoting handle 120 about the pivot point defined by pin opening 223 and pin 233. Handle 120 may pivot relative to wire housing 230 in response to applying a force (e.g., downward, upward, etc.) at grasping feature 112, and more particularly by moving a hand of the user. In this instance, joint 236 may move with grasping feature 112 in a first direction relative to wire housing 230. With articulation wire 170 secured to joint 236, first actuator 210 may be configured to move articulation wire 170 relative to wire housing 230, shaft 140, and articulation joint 150.

First actuator 210 may pull articulation wire 170 proximally to apply a proximal (pulling) force onto clevis 161, thereby causing articulation joint 150 to bend. It should be appreciated that first actuator 210 may be configured to pull articulation wire 170 proximally in response to handle 120 pivoting in multiple directions (e.g., downward, upward, etc.) relative to wire housing 230. That is, with medical device 200 including a single articulation wire 170, actuation of first actuator 210 and handle 120 in either direction provides movement of articulation wire 170 in the same direction. In this instance, end effector 160 may be deflected in the first direction, i.e. the same direction of movement as first actuator 210 and handle 120 relative to wire housing 230. A user of medical device 200 may selectively adjust a degree of articulation of articulation joint 150, and the corresponding extent of deflection of end effector 160, in response to a degree of movement of handle 120 relative to wire housing 230. First actuator 210 and handle 120 may be rotated to move end effector 160 relative to the target treatment site to facilitate further movement of medical device 200 toward the target object.

Still referring to FIG. 8B, second actuator 130 may be actuated to transition end effector 160 from an unactuated state (FIG. 8A) to an actuated state. For example, a user of medical device 200 may move second actuator 130 relative to handle 120 by sliding spool 132 through slot 126. Second actuator 130 may translate over handle 120 in response to applying a force (e.g., proximal, distal, etc.) on spool 132. Second actuator 130 may pull actuation wire 172 proximally to apply a proximal (pulling) force onto the plurality of links 162A, 162B, thereby causing jaws 166A, 166B to engage one another. In this instance, end effector 160 clamps against a target object (e.g., tissue) positioned between jaws 166A, 166B. A user of medical device 200 may selectively adjust a degree of engagement between jaws 166A, 166B in response to an extent of translation of spool 132.

Figure 9:
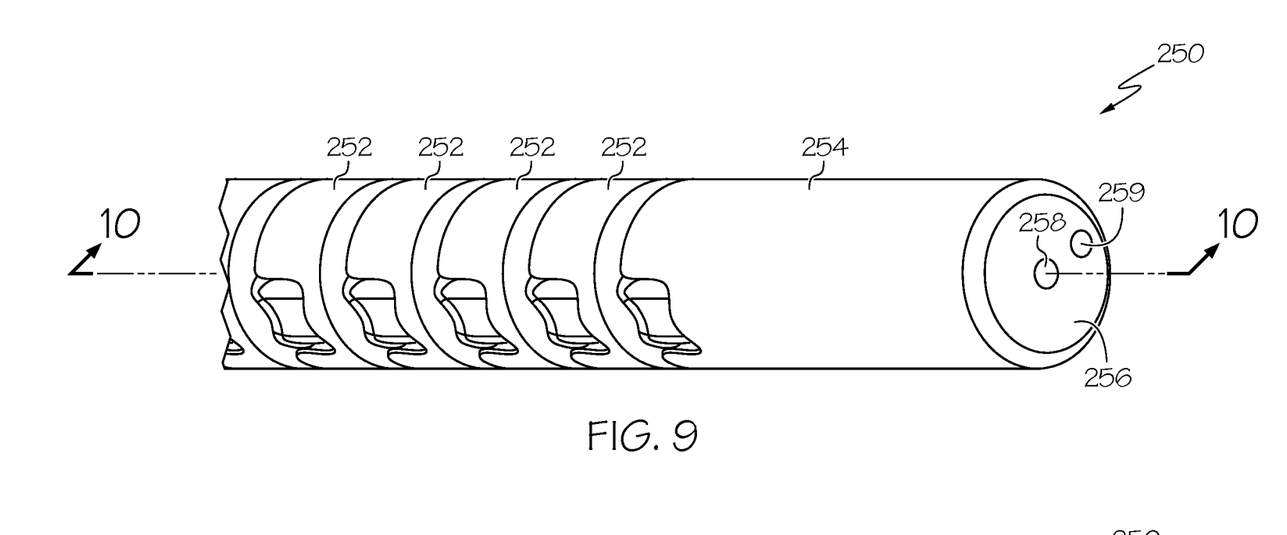
FIG. 9 is a perspective view of an exemplary articulation joint of the medical device of FIGS. 1 and 8A, according to aspects of this disclosure.
Figure 10:
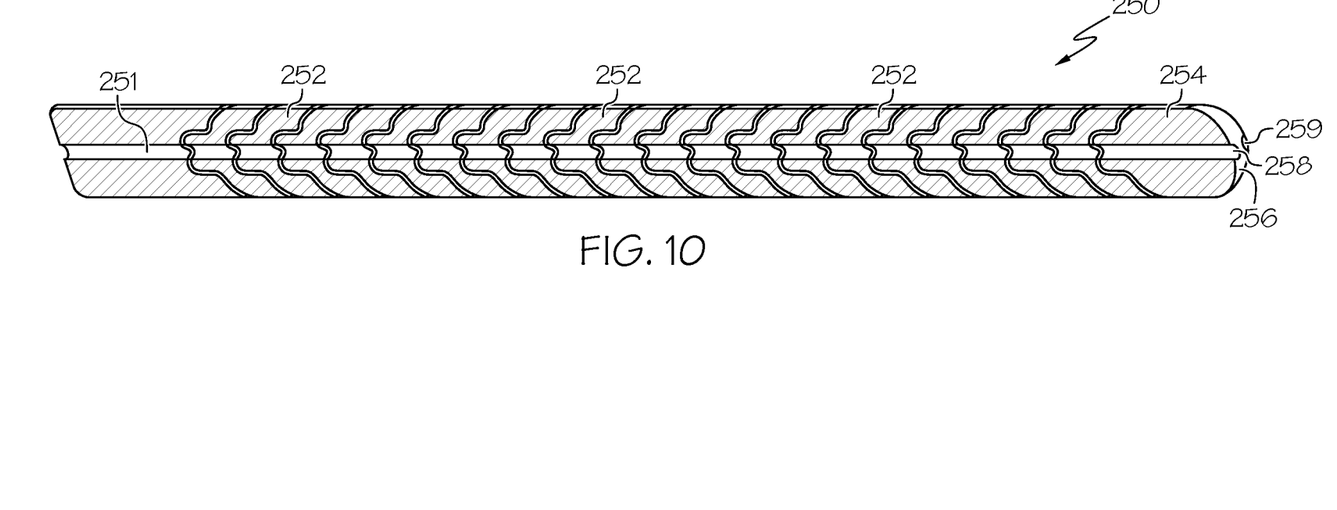
FIG. 10 is a cross-sectional perspective view of the articulation joint of FIG. 9, according to aspects of this disclosure.

FIGS. 9-10 show another exemplary articulation joint 250 according to an example of the disclosure. Except as otherwise described herein, articulation joint 250 may be configured similar to articulation joint 150 described above. It should be understood that articulation joint 250 may be readily incorporated into medical devices 100, 200 described above. Articulation joint 250 may include a plurality of links 252 including a distalmost link 254. Each of the plurality of links 252 may be at least partially received within an adjacent link 252. In this instance, the plurality of links 252 may be nested within one another. The distalmost link 254 may include an actuation opening 258 and an articulation opening 259 at a distal face 256 of the distalmost link 254. It should be appreciated that the articulation lumen 259 may be off-centered to provide a bending force for articulating articulation joint 250.

As seen in FIG. 10, articulation joint 250 may include an actuation lumen 251 extending through each of the plurality of links 252 and the distalmost link 254. Actuation lumen 251 may be aligned with, and terminate at, actuation opening 258. Further, actuation lumen 251 may be sized, shaped, and configured to receive actuation wire 172. Actuation wire 172 may extend outwardly from actuation lumen 251, and distally of distalmost link 254, via actuation opening 258. Although not shown, distalmost link 254 may be coupled to and/or received in clevis 161 (see FIG. 2) and actuation wire 172 may extend through clevis 161 and attach to jaws 166A, 166B.

Articulation joint 250 may further include an articulation lumen extending through each of the plurality of links 252 and the distalmost link 254. The articulation lumen may be aligned with, and terminate at, articulation opening 259. The articulation lumen may be sized, shaped, and configured to receive articulation wire 170. Accordingly, articulation wire 170 may extend outwardly from the articulation lumen, and distally of distalmost link 254, via articulation opening 259 to couple to clevis 161.

Still referring to FIGS. 9-10, the plurality of links 252 and the distalmost link 254 may provide enhanced maneuverability of articulation joint 250. Particularly, the plurality of links 252 and the distalmost link 254 define a plurality of deflection points along a longitudinal length of articulation joint 250, with at least one deflection point formed between an adjacent pair of links 252. Accordingly, articulation joint 250 provides an enhanced articulating radius. It should be appreciated that articulation joint 250 may be configured to articulate, and deflect end effector 160 secured to distalmost link 254, with a greater degree of lateral motion than articulation joint 150. The plurality of links 252 and distalmost link 254 may include a greater wall thickness than articulation joint 150, such that articulation joint 250 may provide greater strength for lifting a target object (e.g., tissue).

Each of the aforementioned systems, devices, assemblies, and methods may be used to manipulate target tissue with enhanced degree of maneuverability. By providing a medical device with an intuitive and ergonomic handle interface capable of controlling an actuation and articulation of an end effector with a single hand, a user may utilize another hand to control other devices and/or tools during a procedure for treating the target site. In this instance, a user may reduce overall procedure time, increase efficiency of procedures, and/or avoid unnecessary harm to a subject's body caused by limited control of the other tools/devices.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical device, comprising:
   a handle that includes a pair of pins positioned on opposing surfaces at a proximal end of the handle and extending radially inward relative to a longitudinal axis of the handle;
   a shaft extending distally from the handle;
   an end effector extending distally from the shaft;
   a first actuator coupled to the handle and secured to a first wire, wherein the first actuator includes:
      a housing that includes a first channel and a distal opening, wherein the first channel is configured to receive a proximal portion of the first wire extending distally from the housing and through the distal opening, and
      a distal extension that includes a pair of sidewalls, and a pair of pin openings formed in opposing surfaces of the pair of sidewalls; and
   a second actuator coupled to the handle and secured to a second wire, wherein the second actuator is received within a slot of the handle, wherein the second wire extends through the shaft and is coupled to the end effector,
   wherein the pair of pins of the handle and the pair of pin openings of the first actuator define a pivot point, such that the first actuator is pivotably coupled to the handle about the pivot point;
   wherein the first actuator is configured to deflect the end effector to a deflected configuration relative to the shaft in response to pivoting a proximal portion of the first channel towards a proximal direction about the pivot point, and the first actuator is configured to return the end effector to an undeflected configuration relative to the shaft in response to pivoting the proximal portion of the first channel towards a distal direction about the pivot point,
   wherein the second actuator is configured to translate relative to the slot of the handle to pull the second wire proximally to actuate the end effector.

2. The medical device of claim 1, wherein the first channel is angled relative to a longitudinal axis of the handle in the undeflected configuration, such that the first wire is positioned within the housing at the angle relative to the longitudinal axis.

3. The medical device of claim 2, wherein the distal opening is aligned with the first channel, and the distal opening has a height that permits vertical movement of the first wire relative to the distal opening.

4. The medical device of claim 3, wherein the handle includes a second channel and a proximal opening; and
   wherein the second channel is aligned with the first channel and receives the first wire through the proximal opening.

5. The medical device of claim 4, wherein the proximal opening includes a height that permits vertical movement of the first wire relative to the proximal opening.

6. The medical device of claim 5, wherein the proximal opening includes a tapered configuration such that a size of the proximal opening decreases from a proximal end to a distal end of the proximal opening.

7. The medical device of claim 4, wherein the first actuator is configured to translate the first wire through the second channel in response to pivoting the first channel relative to the handle.

8. A medical device, comprising:
   a handle;
   a shaft extending distally from the handle;
   an end effector at a distal end of the shaft;
   a first actuator including a housing that includes a first channel, and a distal opening aligned with the first channel, wherein the first channel is configured to receive a proximal portion of a first wire extending distally from the housing and through the distal opening, and wherein the first channel is formed on an outer surface of the housing such that a side of the first channel is open; and
   a second actuator including a second wire disposed within the shaft, wherein the second actuator is slidable relative to the handle;
   wherein the first actuator is configured to retract the first wire proximally relative to the shaft to deflect the end effector, and the first actuator is configured to deflect the end effector to a deflected configuration relative to the shaft in response to pivoting a proximal portion of the first channel towards a proximal direction about a pivot point, and the first actuator is configured to return the end effector to an undeflected configuration relative to the shaft in response to pivoting the proximal portion of the first channel towards a distal direction about the pivot point, wherein, in the undeflected configuration, the first channel is angled relative to a longitudinal axis of the handle; and
   wherein the second actuator is configured to retract the second wire proximally relative to the shaft to move the end effector from an open configuration to a closed configuration.

9. The medical device of claim 1, wherein the first actuator includes a protrusion configured to abut against the handle pivoting relative to the shaft to limit an extent of movement of the first channel relative to the shaft;
   wherein the extent of movement of the first channel defines an extent of deflection of the end effector relative to the shaft.

10. The medical device of claim 8, wherein the handle includes a slot extending along a longitudinal length of the handle, and the second actuator is configured to translate proximally and distally through the slot;
    wherein the second actuator is configured to move the end effector from the open configuration to the closed configuration in response to translating proximally through the slot, and from the closed configuration to the open configuration in response to translating distally through the slot.

11. A medical device, comprising:
    a handle including:
       a proximal extension that includes a pair of pins positioned on opposing surfaces of the proximal extension and extending radially inward relative to a longitudinal axis of the handle; and
       a slot extending along the longitudinal axis and distal of the pair of pins;
    a shaft extending distally from the handle;
    an end effector coupled to a distal end of the shaft;
    a first actuator including:
       a housing that includes a first channel secured to a first wire extending distally from the housing through a distal opening aligned with the first channel; and
       a distal extension that includes a pair of sidewalls, and a pair of pin openings formed in opposing surfaces of the pair of sidewalls; and a second actuator disposed in the slot of the handle and secured to a second wire;

wherein the first wire and the second wire respectively extend through the shaft and are respectively coupled to the end effector;

wherein the pair of pins of the handle and the pair of pin openings of the first actuator define a pivot point, such that the first actuator is pivotably coupled to the handle about the pivot point proximal of the distal opening of the housing;

wherein the pair of sidewalls of the first actuator at least partially define the distal opening aligned with the first channel of the housing at a distal end of the first actuator;

wherein the first actuator is configured to deflect the end effector to a deflected configuration relative to the shaft in response to pivoting a proximal portion of the first channel towards a first direction about the pivot point, and the first actuator is configured to return the end effector to an undeflected configuration relative to the shaft in response to pivoting the proximal portion of first channel towards a second direction about the pivot point opposite the first direction.

12. The medical device of claim 11, wherein the second actuator is configured to translate proximally and distally through the slot of the handle, and wherein the second actuator is configured to retract the second wire proximally relative to the shaft to move the end effector from an open configuration to a closed configuration.

13. The medical device of claim 11, wherein the first actuator includes a proximal extension positioned opposite the distal extension, wherein the proximal extension includes a grasping feature positioned at a proximal end of the first actuator.

14. The medical device of claim 11, wherein the distal opening of the first actuator has a shape and dimension that permits movement of the first wire relative to the distal opening.

15. The medical device of claim 11, wherein the first actuator includes a protrusion configured to abut against a proximal end of the handle to limit an extent of movement of the first channel relative to the shaft, wherein the extent of movement of the first channel defines an extent of deflection of the end effector relative to the shaft.

16. The medical device of claim 11, wherein the second actuator is configured to move the end effector from a closed configuration to an open configuration in response to distal translation of the second actuator through the slot of the handle.

17. The medical device of claim 11, wherein the first channel is formed on an outer surface of the housing such that the first channel has an open outer side.

18. The medical device of claim 11, wherein the slot of the handle includes a proximal opening that is positioned distal of the pivot point relative to the longitudinal axis, and wherein the proximal opening of the slot is configured to receive the first wire therein.

19. The medical device of claim 11, wherein the first channel is angled relative to the longitudinal axis of the handle in the undeflected configuration, such that the first wire is positioned within the housing at an angle relative to the longitudinal axis.

* * * * *